United States Patent
Ito

[11] 4,176,920
[45] Dec. 4, 1979

[54] OPHTHALMOSCOPIC SYSTEM WITH A WIDE ANGLE OBJECTIVE LENS

[75] Inventor: Yuji Ito, Chigasaki, Japan

[73] Assignee: Canon Kabushiki Kaisha, Tokyo, Japan

[21] Appl. No.: 797,636

[22] Filed: May 17, 1977

[30] Foreign Application Priority Data

May 19, 1976 [JP] Japan ................................ 51-57466

[51] Int. Cl.$^2$ .............................................. A61B 3/14
[52] U.S. Cl. ........................................ 351/7; 350/189; 351/16; 354/62
[58] Field of Search ................. 351/7, 6, 16; 350/189; 354/62

[56] References Cited

U.S. PATENT DOCUMENTS 3,594,071  7/1971  Okajima .................................... 351/7
3,914,032  10/1975  Takano et al. ........................ 351/6 X Primary Examiner—Paul A. Sacher
Attorney, Agent, or Firm—Toren, McGeady and Stanger

[57] ABSTRACT

The wide angle ophthalmoscopic system disclosed includes an objective lens group having a forward direction toward an eye to be examined and having at least one meniscus lens and a positive lens. The meniscus lens includes a front concave forward surface and constitutes substantially an aplanatic lens having an aplanatic point to be situated in the front part of an eye to be examined. A converging lens group in the system is positioned behind the objective lens group. An illuminating system has at least one light source and light transmitting arrangement for directing light in the forward direction. An observing optical system is optically aligned with the objective lens group for transmitting images formed by the objective lens group.

11 Claims, 10 Drawing Figures

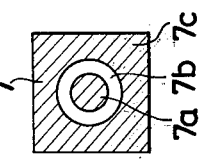
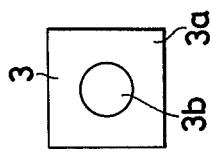
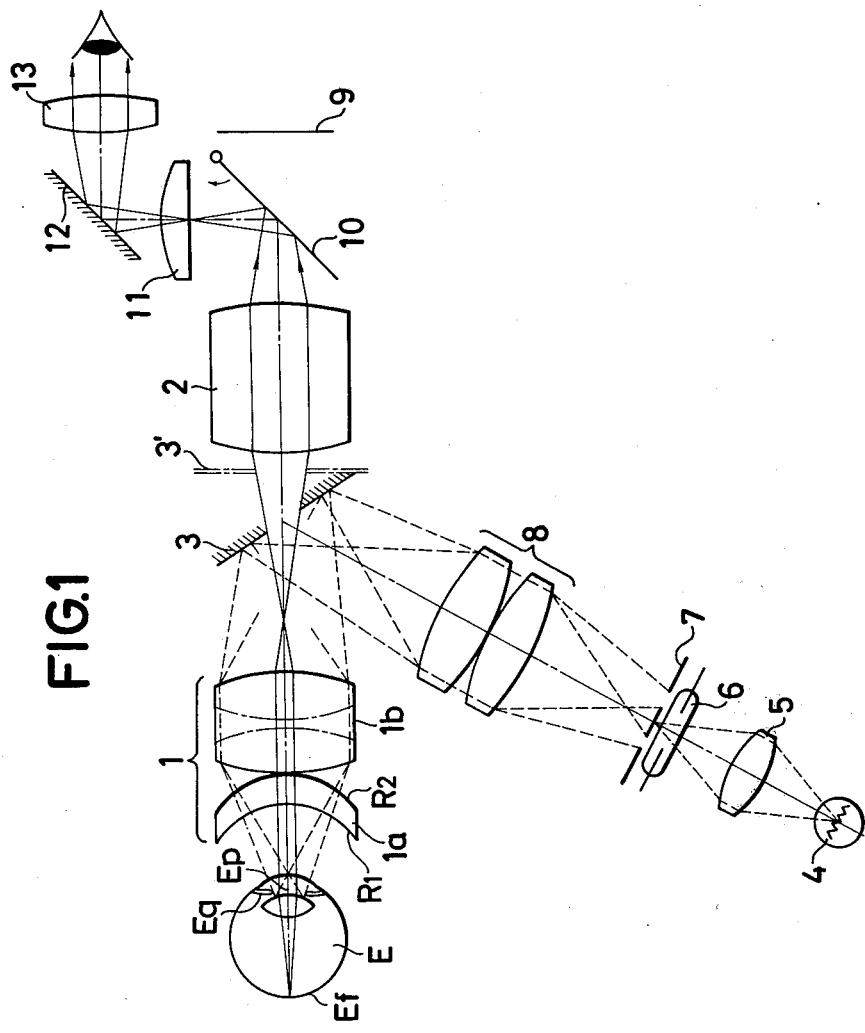

OPHTHALMOSCOPIC SYSTEM WITH A WIDE ANGLE OBJECTIVE LENS

BACKGROUND OF THE INVENTION

This invention relates to ophthalmoscopes and ophthalmoscopic cameras, and more particularly to improvements of an objective lens for use in such ophthalmoscope or ophthalmoscopic camera.

Most of the ophthalmoscopic cameras which have found wide acceptance are designed to have an objective lens comprised of a positive meniscus lens convex toward an eye to be examined with limitation of its view angle to about 30 degrees. To increase the image angle up to about 45 degrees, it is known to make use of a biconvex lens as the objective lens. It has also been proposed by the present applicant to construct the objective lens from a positive meniscus lens concave toward an eye to be examined and a positive meniscus lens concave toward an image thereof as described in U.S. Pat. No. 3,914,032.

With the objective lens having an increased view angle, it is desired to reduce astigmatism. Incorporation of an apertured mirror as arranged between the objective lens and an image forming lens to reflect the illuminating light rays from a light source in the direction of the optical axis of the eye leads to a further requirement of increasing the relative aperture of the objective lens, while still minimizing spherical aberration and coma thereof. As the objective lens is positioned in the path of the illuminating light rays, there is some possibility of producing disturbing light reflection due to the light rays reflected from the surfaces of the objective lens to the film plane.

SUMMARY OF THE INVENTION

The present invention has for its general object to provide an ophthalmoscopic system with an objective lens having an increased angle of view without causing production of unduly large aberrations. Whilst the conventional objective lens described in U.S. Pat. No. 3,914,032 has an angle of view not exceeding 45 degrees, two specific embodiments of the present invention to be described later are to provide for view angles of 60 degrees and 80 degrees. According to the present invention, the achievement of such a large increase in the angle of view is realized by designing at least one positive meniscus lens element of concavity toward an eye to be examined in the objective lens to aplanatic configuration, or likewise configuration to an aplanatic lens element. In this connection, it should be noted that the positive meniscus lens shown in U.S. Pat. No. 3,914,032 is designed not so much complicated but to the simple positive meniscus lens configuration known in the art.

BRIEF DESCRIPTION OF THE DRAWINGS

FIG. 1 is a schematic sectional view of one embodiment of an ophthalmoscopic system according to the present invention.

FIGS. 2 and 3 are plan views of an apertured illuminating mirror and a ring-shaped diaphragm usable in the system of FIG. 1.

DESCRIPTION OF THE PREFERRED EMBODIMENTS

Figure 4:
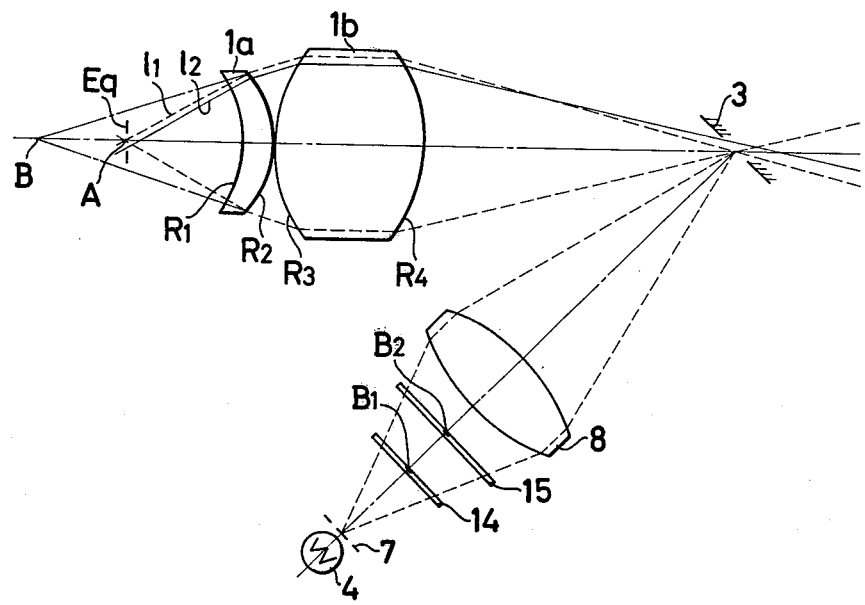
FIG. 4 is a fragmentary sectional view of the system of FIG. 1.

Referring to FIGS. 1 to 7 and first to FIG. 1, there is shown one embodiment of an ophthalmoscopic system according to the present invention including an objective lens group 1 and an image-forming lens group 2 aligned along a common optical axis of an eye E so that an image of the ocular fundus Ef to be examined is either to be formed at a film plane 9 with a tiltable mirror 10 set in its non-viewing position, or to be viewed through a field lens 11, a reflection mirror 12 and an eye-piece 13, as the tiltable mirror 10 is set in the illustrated position.

Positioned in an air space between the objective lens group 1 and the image-forming lens group 2 is an illuminating mirror 3 inclined to the optical axis of the eye E and reflecting the illuminating light rays from an illuminating optical arrangement in the direction of the optical axis of the eye E. The illuminating mirror 3 contains a central aperture 3b for the passage of image forming rays, in known manner as shown in FIG. 2, with the remaining area 3a being fully mirrored. The illuminating optical arrangement is disposed with its optical axis declined from the optical axis of the eye E and comprises a tungsten lamp 4 as a first light source extending transversely to the optical axis, a condenser lens 5, a strobotube 6 as a second light source extending transversely to the optical axis, a ring-shaped diaphragm 7 positioned adjacent the strobotube 6 and in conjugate relation to the first light source or tungsten lamp 4 with respect to the condenser lens 5, and a relay lens 8 arranged so that the ring-shaped diaphragm 7 is conjugate to the apertured illuminating mirror 3 with respect to the relay lens 8. The details of the ring-shaped diaphragm are shown in FIG. 3, wherein a central obscuring diaphragm element 7a and an apertured diaphragm element 7c are concentrically disposed on a single transparent substrate not shown with the resulting opening being of a ring-shape so that an outer annular zone of a pupil Ep of an iris Eq in the eye E is illuminated, as the apertured mirror 3 is almost conjugate to the pupil Ep with respect to the objective lens group 1. Although the apertured mirror 3 serves as a diaphragm for the image forming rays, a diaphragm may be used as located at 3'.

The objective lens group 1 comprises a positive meniscus lens 1a concave toward the eye E and a biconvex lens 1b which may be in the form of a singlet but preferably of a cemented triplet of achromatism. The image-forming lens group 2 comprises a plurality of singlets. According to the present invention, while the front surface $R_1$ of the positive meniscus lens 1a is a spherical surface with its center of curvature being coincident with the center A of the pupil Ep (see FIG. 4), the rear surface $R_2$ is configured to an aplanatic surface relative to the center A of the pupil Ep. Letting S denote the axial separation between the pupil center A and a point at which the surface $R_2$ intersects the optical axis, and S' the axial separation between that point and an aplanatically conjugate point which is designated by B in FIG. 4, then we have $S'/S=n$, wherein n is the index of refraction of the material from which the positive meniscus lens is made. With this lens configuration, there is no spherical aberration and no coma from the front and rear surfaces $R_1$ and $R_2$ and also no astigmatism from the rear surface $R_2$, provided that the object point is located in coincidence with the pupil center A. To facilitate aberrational correction in the extended range of view angles, it is preferred that the rear surface $R_4$ of the biconvex lens 1b is made aspherical as known in the art. For a further increase in the view angle, the both surfaces of the biconvex lens 1b are formed to aspherical surfaces.

Another advantage deriving from the employment of the aplanatic lens 1a is that, as a ray of light $l_1$ emanating from the pupil center A is not subjected to refraction at the front surface $R_1$ and is refracted by the rear surface $R_2$ as if it emanate from the aplanatically conjugate point B, the angle of inclination of the incident light ray on the front surface $R_3$ of the biconvex lens can be gradually decreased.

As the objective lens group constitutes part of a photographic optical system with its diaphragm coinciding with the iris Eq, a light ray $l_1$ passing through the opening of the iris Eq at the center thereof becomes a principal light ray. And a bundle of light rays including ones $l_1$ and $l_2$ as marginal rays contributes as a part to the image forming rays which are projected by the (image-forming) lens the group 2 onto the film plane 9. In this case, the front surface $R_1$ does not produce any coma and astigmatism, because the diaphragm is located at the center of curvature of the front surface $R_1$. It will be understood from the above that a large increase in the view angle of the ophthalmoscopic system can be achieved by designing the positive meniscus lens 1a in the form of an aplanatic lens, or likewise lens having a similar function to that of the aplanatic lens, while nevertheless preserving a high level of aberrational correction over the extended range of view angles.

A specific example of the objective lens group having only one positive meniscus lens as shown in FIG. 4 with a view angle of 60 degrees may be constructed in accordance with the numerical data given in Table 1 below. In the table, the radii of curvature, R, and the axial thicknesses and separations, D, numbered consecutively from front to rear are given along with the corresponding indices of refraction for the spectral D line of sodium and the Abbe numbers for the various lens elements. The minum values of the radii, R, indicate surfaces concave toward front.

Table 1

| f = 100 (mm) | 2ω = 60° (view angle) F 1 : 1 | | |
|---|---|---|---|
| $R_1 = -96.05$ | | | |
| | $D_1 = 24.01$ | Nd = 1.617 | Vd = 62.8 |
| $R_2 = -74.19$ | | | |
| | $D_2 = 0.1$ | | |
| $R_3 = 124.87$ | | | |
| | $D_3 = 124.87$ | Nd = 1.617 | Vd = 62.8 |
| $R_4 = -124.87$ | (aspherical) | | |

Figure 5:
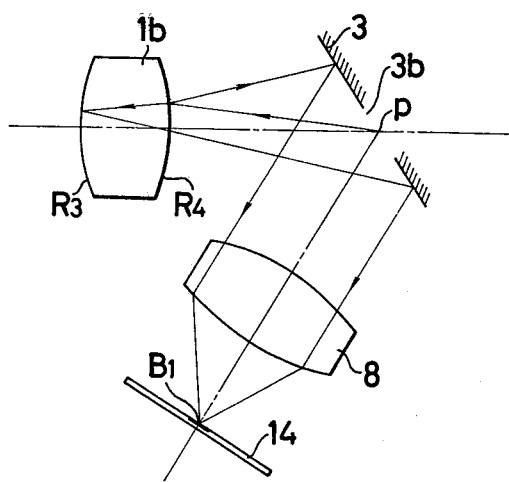
FIG. 5 is a diagram of geometry considered in defining the location of a black spot for freedom from disturbing light reflections according to the prior art.

As the objective lens group 1 is illuminated, some of the illuminating light rays are reflected from the lens surfaces in the group 1 to the central hole 3b of the illuminating mirror 3 which must be kept free from disturbing incident light as the hole 3b serves for the passage of image forming rays. It is known to eliminate disturbing light reflections on the surfaces $R_3$ and $R_4$ of the biconvex lens element in the group 1 by making use of a black spot $B_1$ arranged at a point between the light source and the relay lens 8 coaxially on the optical axis of the illuminating optical arrangement as shown in FIG. 5. This is also disclosed in U.S. Patent application Ser. No. 658,874 now U.S. Pat. No. 4,098,549 assigned to the assignee of the present invention. The location and size of the black spot $B_1$ are defined as follows. A light ray emerging from a point P on the plane of the illuminating mirror 3 in the area of the hole 3b is either reflected from, or refracted by the rear surface $R_4$ of the biconvex lens 1b to the mirror 3, or to the front surface $R_3$ respectively. The reflected ray from the mirror 3 is converged by the relay lens 8, while the refracted ray after successive reflections from the front surface $R_3$ and from the mirror 3 is also converged by the same relay lens 8. The convergence points for the reflected and refracted rays can be brought into coincidence with each other by suitable selection of the radii of curvature of the front and rear surfaces $R_3$ and $R_4$ and the axial thickness of the lens 1b. In practice, the black spot $B_1$ may be formed on a transparent plate 14.

Figure 6:
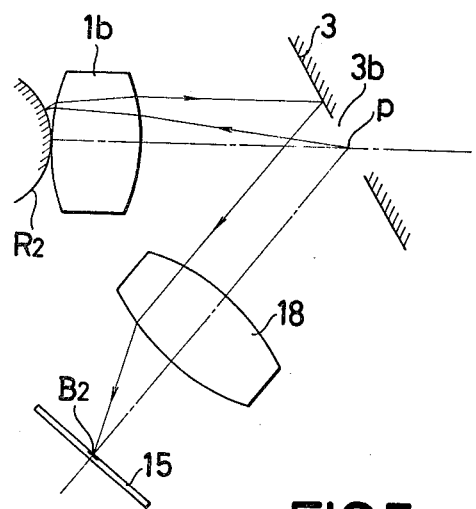
FIGS. 6 and 7 are similar views showing a method of eliminating the disturbing light reflections from the objective lens according to the present invention.

FIG. 6 shows a method of determining the location and size of an additional black spot $B_2$ for eliminating disturbing light reflections on the rear surface $R_2$ of the positive meniscus lens 1a. In this case, the black spot $B_2$ is conjugate to the hole 3b of the illuminating mirror 3 with respect to a particular optical arrangement consisting of the aplanatic surface $R_2$, the biconvex lens 1b, the reflecting surface 3a of the illuminating mirror 3 and the relay lens 8, as an ideal light ray emerging from the point P is passed through the biconvex lens 1b to the aplanatic surface $R_2$, then reflected therefrom to the biconvex lens 1b, then goes after passage therethrough to the mirror surface 3a and is then reflected therefrom to the relay lens 8 by which it is converged to the black spot $B_2$ formed on a transparent plate 15.

Figure 7:
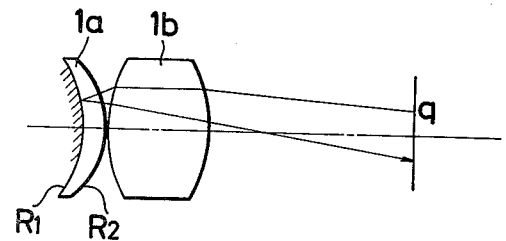

In the case of disturbing light reflections on the front surface $R_1$ of the positive meniscus lens 1a, there is no possibility of its entrance into the hole 3b of the illuminating mirror 3, because, as has been explained in connection with FIGS. 1 and 2, the center of curvature of the front surface $R_1$ coincides with the center of the eye-pupil, and the rear surface $R_2$ is made aplanatic for freedom from aberrations even at wide angles of view. When the front surface $R_1$ is regarded as a mirror surface, therefore, an ideal light ray emerging from an optional point, q, on the mirror 3 which is conjugate to the eye-pupil is converged to a point symmetrical to the point, q, with respect to the optical axis, as shown in FIG. 7.

According to the present invention, therefore, the two black spots $B_1$ and $B_2$ on the respective transparent plates 14 and 15 are employed as arranged in an air space between the light source 4 and the relay lens 8 and extending transversely to the optical axis of the illuminating optical arrangement as shown in FIG. 4 for the purpose of eliminating disturbing light reflections on the objective lens group 1.

Figure 8:
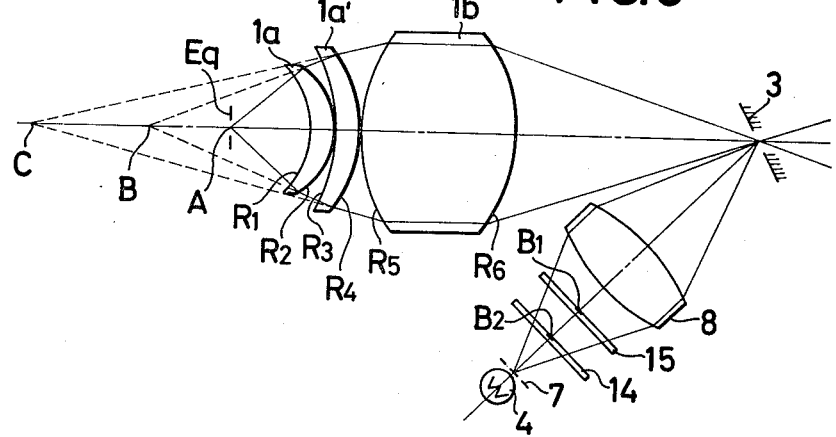
FIG. 8 is a fragmentary schematic sectional view of another embodiment of an ophthalmoscopic system according to the present invention.

FIG. 8 shows another embodiment of the present invention in which two positive meniscus lenses 1a and 1a' are employed as arranged nearer an eye to be examined than a biconvex lens 1b. These two positive meniscus lenses 1a and 1a' are so configured that the front surface R₁ of the front positive meniscus lens 1a has a center of curvature coincident with the center A of an eye-pupil, and the rear surface R₂ is aplanatic with its aplanatically conjugate point at B, and that the front surface R₃ of the second positive meniscus lens 1a' has a center of curvature coincident with the point B, and the rear surface R₄ is aplanatic with an aplanatically conjugate point to the point B being at C. In other words, the first and second positive meniscus lenses 1a and 1a' form an aplanatic broken-contact doublet to the center of the eye-pupil, so that there is no spherical aberration and no coma for the object point at the pupil center A. Further, the surfaces R₂ and R₄ produce no astigmatism. When this objective lens is used for photography, the surfaces R₁ and R₃ produce no coma and no astigmatism provided that the iris position corresponds to the diaphragm position.

A specific example of the objective lens corresponding to that shown in FIG. 8 may be constructed in accordance with the numerical data given in Table 2 below. The various symbols in the table have the meanings described in connection with Table 1.

Table 2

| $f = 100$ (mm) | $2\omega = 80°$ | F 1 : 0.78 | |
|---|---|---|---|
| $R_1 = -83.54$ | | | |
| | $D_1 = 22.28$ | $Nd = 1.617$ | $Vd = 62.8$ |
| $R_2 = -65.39$ | | | |
| | $D_2 = 0.1$ | | |
| $R_3 = -171.39$ | | | |
| | $D_3 = 22.28$ | $Nd = 1.617$ | $Vd = 62.8$ |
| $R_4 = -119.67$ | | | |
| | $D_4 = 0.1$ | | |
| $R_5 = 150.38$ | | | |
| | $D_5 = 150.38$ | $Nd = 1.617$ | $Vd = 62.8$ |
| $R_6 = -150.38$ | (aspherical) | | |

Figure 9:
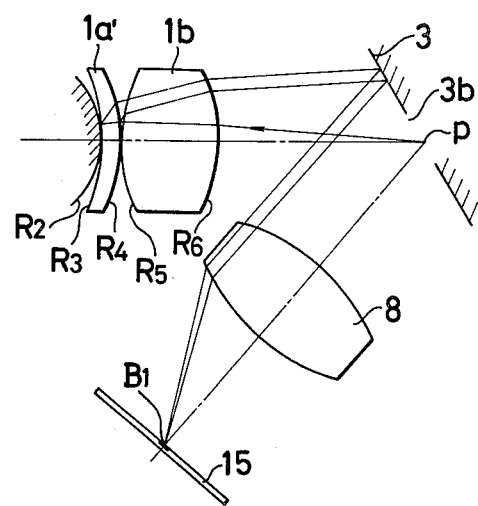
FIG. 9 is a diagram of geometry considered in defining the location of a black spot for freedom from disturbing light reflections from the objective lens of FIG. 8.

The disturbing light reflections on the objective lens of FIG. 8 are also possible with two black spotted plates 14 and 15. In other words, those on the surfaces R₅ and R₆ of the biconvex lens 1b are eliminated by the method shown in FIG. 5, and those on the front surfaces R₁ and R₃ of the first and second positive meniscus lenses 1a and 1a' are removed for the reasons explained in connection with FIG. 7. The elimination of those on the rear surfaces R₂ and R₄ will next be explained by reference to FIG. 9.

For the surface R₄, situation is similar to that shown in FIG. 6. On the other hand, a light ray coming from the point P through the biconvex lens 1b and the second positive meniscus lens 1a' is reflected from the surface R₂ and therefrom directed through the second positive meniscus lens 1a' and the biconvex lens 1b to the mirror 3 by which it is reflected to the relay lens, finally reaching a convergence point. This point can be brought into coincidence with that for the surface R₄ at the black spot B₁ by suitable selection of either the axial thickness of the second positive meniscus lens 1a', or the axial air separation between the surfaces R₂ and R₃, or between the surfaces R₄ and R₅. The size of the black spot B₁ is dependent upon an image of the hole 3b formed on the plate 15 by a particular optical system between the illuminating mirror 3 and the black spotted plate 15 in the path of disturbing incident light. As a single black spot is adopted for elimination of reflexes from two separate reflecting surfaces, it is of course required that a larger size of black spot be selected from two different ones.

Figure 10:
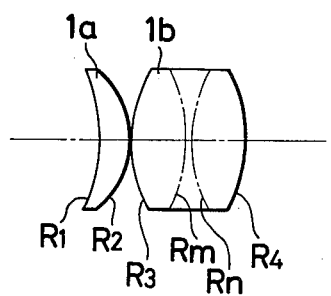
FIG. 10 is a block diagram of the objective lens of the present invention in which the biconvex lens comprises a plurality of elements cemented together.

If the biconvex lens 1b is constructed in the form of a cemented triplet as shown in FIG. 10, disturbing light reflections on the cemented surfaces Rm and Rn must be taken into account. In this case, those on the surface Rm is simultaneously eliminated with those on the surface R₂ in a manner similar to that shown in connection with the surfaces R₃ and R₄ of FIG. 9. The surface Rn may be designed in relation to the surfaces R₃ and R₄ for elimination of reflection. The number of black spots necessary to eliminate disturbing light reflections is equal to that of the lens surfaces in the objective lens group 1 with exclusion of those shown in FIG. 7. As has been noted above, however, this number can be largely reduced not only by suitable selection of the lens thicknesses and/or axial air separations, but also by adjusting the size of each black spot to a somewhat larger level than the theoretical one.

It will be seen from the foregoing that the present invention provides an ophthalmoscopic system with a remarkably increased angle of view without causing production of unduly large aberrations over the extended view angle range. The positive lens located on the image side of the aplanatic lens is formed to biconvex configuration, thereby giving an additional advantage of increasing design flexibility for power distribution and aberrational correction, as both of the entrance and exit surfaces of the eye convex lens act in converging manner. A furthermore advantage of the invention is to facilitate elimination of disturbing light reflections.

What is claimed is:

1. An ophthalmoscopic system provided with a wide angle objective lens comprising;
   an objective lens group opposed to a human eye and including at least one meniscus lens and positive lens, and said meniscus lens having a front surface concave to the human eye and being substantially an aplanatic lens having an aplanatic point, the aplanatic point being situated in the front part of the human eye;
   a converging lens group positioned in rear of said objective lens group;
   an illuminating system having at least one light source and light transmitting means, and the light emergent section of this system being directed toward the human eye; and
   an observing optical system having said objective lens group and image transmitting means.

2. An ophthalmoscopic system as described in claim 1, wherein said objective lens group consists of a positive meniscus lens and a biconvex lens.

3. An ophthalmoscopic system as described in claim 1, wherein said objective lens group consists of two positive meniscus lenses and a biconvex lens.

4. An ophthalmoscopic system as described in claim 1, wherein said light transmitting means has reflecting means and a plurality of lenses, and said reflecting means is positioned between the human eye and said converging lens group.

5. An ophthalmoscopic system as described in claim 1, wherein said light transmitting means has a mirror and lens means, an aperture stop is arranged between the reflecting plane of the mirror and said converging lens group, and a light obscuring spot is arranged in conjugate relation to the aperture of said stop with respect to said positive lens, the aplanatic surface serving as a mirror surface, said positive lens, said reflecting plane and lens means.

6. An ophthalmoscopic system provided with a wide angle objective lens comprising;
   at least one positive aplanatic meniscus lens concave to a human eye, a biconvex lens arranged adjacent and in rear of said positive meniscus lens, followed by an image forming lens group, and followed by a photographic film;
   an apertured mirror arranged between said biconvex lens and said image forming group;
   a relay lens and a light-impermeable spot between a photographic light source and the apertured mirror, said light-impermeable spot and the aperture opening of said apertured mirror as well as said biconvex lens being conjugate in respect of the rear surface of said positive aplanatic meniscus lens with said biconvex lens and the mirror portion of said apertured mirror and said relay lens.

7. A wide angle opthalmoscopic system for examining an eye comprising:
   an objective lens group having a forward direction toward an eye to be examined, said group having at least one meniscus lens and a positive lens, said meniscus lens having a front concave forward surface, said meniscus lens being substantially an aplanatic lens having an aplanatic point to be situated in the front part of an eye to be examined;
   a converging lens group positioned behind said objective lens group;
   an illuminating system having at least one light source and light transmitting means for directing light in the forward direction; and
   an observing optical system optically aligned with said objective lens group for transmitting images formed by said objective lens group.

8. A system as in claim 7, wherein said objective lens group consists of a positive meniscus lens and a biconvex lens.

9. A system as in claim 7, wherein said objective lens group consists of two positive meniscus lenses and a biconvex lens.

10. A system as in claim 7, wherein said light transmitting means includes reflecting means and a plurality of lenses, said reflecting means being positioned between the converging lens group and the objective lens group.

11. A system as in claim 7, wherein said light transmitting means has lens means and a mirror with a reflecting plane, an aperture stop between the reflecting plane of the mirror and said converging lens group, and a light obscuring spot in conjugate relation to the aperture of said stop with respect to said positive lens, said aplanatic surface serving as a mirror surface, said positive lens, said reflecting plane and said lens means.

* * * * *